US008727987B2

(12) United States Patent
Chauhan

(10) Patent No.: US 8,727,987 B2
(45) Date of Patent: May 20, 2014

(54) MECHANICAL MANIPULATOR FOR HIFU TRANSDUCERS

(75) Inventor: Sunita Chauhan, Singapore (SG)

(73) Assignee: Nanyang Technological University, Singapore (SG)

( * ) Notice: Subject to any disclaimer, the term of this patent is extended or adjusted under 35 U.S.C. 154(b) by 2047 days.

(21) Appl. No.: 11/579,542

(22) PCT Filed: May 6, 2005

(86) PCT No.: PCT/SG2005/000143
§ 371 (c)(1),
(2), (4) Date: Aug. 11, 2008

(87) PCT Pub. No.: WO2005/107622
PCT Pub. Date: Nov. 17, 2005

(65) Prior Publication Data
US 2008/0312561 A1    Dec. 18, 2008

Related U.S. Application Data

(60) Provisional application No. 60/568,252, filed on May 6, 2004.

(51) Int. Cl.
*A61N 7/00* (2006.01)
(52) U.S. Cl.
USPC ............................ 600/439; 600/407; 600/437
(58) Field of Classification Search
USPC .................................. 600/407–480; 601/1–4
See application file for complete search history.

(56) References Cited

U.S. PATENT DOCUMENTS

| 4,604,016 | A | | 8/1986 | Joyce |
| 4,671,256 | A | | 6/1987 | Lemelson |
| 5,105,367 | A | * | 4/1992 | Tsuchihashi et al. ......... 700/264 |
| 5,876,325 | A | * | 3/1999 | Mizuno et al. ................ 600/102 |
| 6,080,181 | A | * | 6/2000 | Jensen et al. .................. 606/205 |
| 6,711,436 | B1 | * | 3/2004 | Duhaylongsod .................. 607/9 |

FOREIGN PATENT DOCUMENTS

| EP | 0 326 768 A2 | 8/1989 |
| WO | WO-97/29690 A1 | 8/1997 |
| WO | WO-0220084 A2 | 3/2002 |

OTHER PUBLICATIONS

Davies et al., "A Robotic Approach to HIFU Based Neurosurgery," Lecture Notes in Computer Science, 1496, pp. 386-396, Springer Verlag, Oct. 1988.
Sunita Chauhan, "A Mechatronic System for Non Invasive Treatment of the Breast Tissue," Mechatronics and Machine Vision 2002: current practice, Research Studies Press Ltd., pp. 359-366.
Chauhan et al., "High-Intensity-Focused-Ultrasound (HIFU) Induced Homeostasis and Tissue Ablation," BiOS'03, Photonics West, SPIE, Jan. 25-31, 2003, 4954-25.

* cited by examiner

*Primary Examiner* — Tse Chen
*Assistant Examiner* — Vani Gupta
(74) *Attorney, Agent, or Firm* — Birch, Stewart, Kolasch & Birch, LLP

(57) ABSTRACT

A mechanical manipulator (10) for controlling the movement of high intensity focused ultrasound (HIFU) transducers, especially for medical use, such as in the treatment of cancers. A base harness having two or three legs (12) is mounted on the treatment table. A central shaft mounted on the base harness carries a diagnostic probe as well as a plurality of treatment probes. The treatment probes may be moved through three degrees of freedom using computer controlled motors. The treatment probes may be moved linearly, in jaw motion and in a pitch motion.

25 Claims, 9 Drawing Sheets

MECHANICAL MANIPULATOR FOR HIFU TRANSDUCERS

RELATED APPLICATIONS

This International Phase PCT application claims priority from U.S. Provisional Application 60/568,252, filed May 6, 2004, priority of which is claimed and which is hereby incorporated by reference.

TECHNICAL FIELD

The present invention relates to a mechanical manipulator for high intensity focused ultrasound (HIFU) transducers. In particular, it relates to a computer controlled mechanical device for positioning HIFU transducers during medical procedures for the ablation of tissues and cancers.

BACKGROUND ART

The development of minimally invasive and non-invasive surgical techniques have remained a prime research focus in the bio-medical area over the past two decades due to several advantages over conventional surgery methods. Computer-assisted surgery and medical robotics have improved the ways in which surgery has been done in the past. In image-guided surgery, the pre-operative planning scheme is executed using medical images/data, such as CT, MRI, X-Ray or Ultrasound images, gathered prior to the intervention. This information helps the surgeons in simulating, visualizing, guiding and assisting a surgical procedure (1-6).

The applications of robots and computer integration in medicine range from simplistic laboratory robots for tool positioning to highly complex surgical robots that carry out surgical procedures under computer control. Most of the robotic systems for surgery aim at assisting in minimally invasive surgical procedures. One such surgical robot is the da Vinci® surgical system, which has successfully completed hundreds of cardiac, general and other types of procedures. Other notable examples are the AESOP and ZEUS robotic surgical systems.

There are various non-invasive alternatives to various surgical indications, such as microwave, RF, lasers, X-rays, or nuclear radiation exposure, however, a safer and radiation-free modality, known as High Intensity Focused Ultrasound (HIFU) is gaining importance and has shown high potential for treatment of a wide range of medical conditions (7-14). HIFU is a non-invasive technique capable of selective destruction of tissue volumes within the body. HIFU works by producing damage in the focal region of an acoustic beam in a predictable and reproducible manner, while sparing overlying tissue. Studies have shown that cancers/tumors are relatively more receptive to heat and the range of temperatures induced by HIFU has been shown to achieve high localized cytotoxicity. This is a phenomenon that does not occur with microwave or infrared exposure.

The use of ultrasound as a modality for diagnostic imaging in medicine has been well known for more than two decades. Its therapeutic applications, for example in sports medicine (micro-massaging action), cancer treatment (hyperthermia), enhanced chemotherapy (e.g. breach of blood brain barrier by focusing ultrasound to a discrete point), stone disintegration (shock-wave therapy), or tissue ablation (Focal Ultrasound Surgery), opened up a big potential for a wide variety of medical applications. Therapeutic ultrasound is established in the treatment of diverse surgical conditions, such as cataract, liver cancer, and stones, without danger to healthy tissue. The unique properties of ultrasound to be able to achieve tight focus at a given depth and non-invasively target localized tissue structures present significant treatment potential.

Several commercial devices that employ HIFU are available for treating prostate diseases. One such commercial HIFU system is the Sonablate 200™ (Focal Surgery Inc. Milpitas, Calif.), developed in 1992, for the treatment of a common prostate disease, Benign Prostatic Hyperplasia (BPH). In the Sonablate system, a 4-MHz transducer is used for both lesion induction and imaging purposes. Clinical trials of this machine were conducted in Japan and Europe. The device has undergone several modifications since then. Another commercial HIFU system called Ablatherm™ (Technomed International, Lyon, France) utilizes separate transducers, 7.5 MHz for imaging and 2.25 MHz for therapy purposes. This system is also targeted for BPH treatment. Another version of this system called Ablatherm® (EDAP TMS S.A., France) is commercially available for treatment of BPH and prostate cancers.

All of the above mentioned prostate treatment systems are primarily targeted for BPH treatment with only a small percentage of success in prostate cancers without the aid of any adjuvant modality. One reason for the latter could be the preferentially high absorption in the rectal wall, thus allowing less energy to transfer deeper in the tissue. An Israeli company named Insightec, Ltd. has commercialized an image guided non-invasive HIFU surgery system for applications in soft tissues. This system for breast surgery relies on expensive MRI guidance.

One system which has been designed for breast cancer is described in International Publication WO03/059434 published on Jul. 24, 2003. This arrangement utilizes a robotic manipulator which carries a jig assembly including an array of treatment probes and a single diagnostic probe. The probes can be moved by the robotic manipulator in x, y and Θ directions. The diagnostic probe first determines the size of the tumor and the treatment probes are then used to ablate the tumor by the superposition of ultrasonic waves at a con-focal region.

DISCLOSURE OF THE INVENTION

Figure 1:
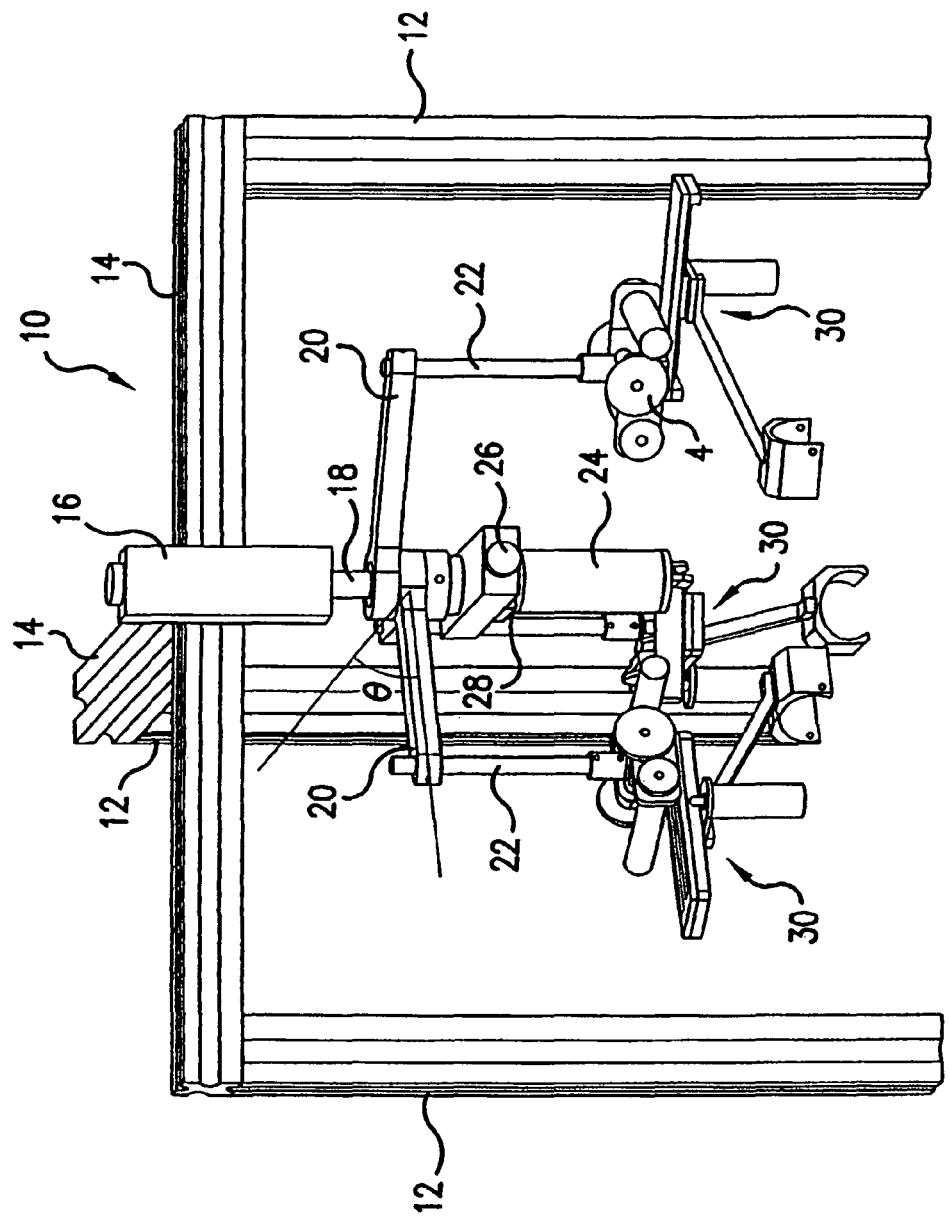
FIG. 1 is a perspective view of the harness and modules of the present invention.

The present invention relates to a mechanical manipulator for ultrasonic transducers which are under supervisory control by the surgeon through a computer. A multiple probe technique and a custom designed robotic manipulator system are disclosed, that can be used for focusing ultrasound energy in the target tissue in order to precisely position multiple ultrasound transducers to focus into deep targets.

The present invention also relates to a mechanical manipulator for HIFU transducers having a plurality of modules for aiming the transducers, including a single diagnostic module and a plurality of treatment modules.

The present invention also relates to a mechanical manipulator for ultrasonic transducers having a base harness from which a diagnostic module and a plurality of treatment modules are centrally mounted.

The present invention also relates to a mechanical manipulator having a plurality of treatment modules, each of which allows movements in three degrees of freedom under supervisory control of the surgeon through a computer. Each module allows the transducer to move linearly under the control of a first motor, with additional motors controlling the yaw and pitch. Each module is mounted from a vertical rod (serving as a common central axis) so that the transducers are originally aimed to a central focal point.

The present invention also relates to a mechanical manipulator for HIFU transducers where a diagnostic probe is originally mounted centrally (it is displaced linearly to acquire multiple images in parallel planes) from a base unit and treatment probes are offset radially from the diagnostic probe.

The present invention can accomplish this using a base harness which is mounted on a treatment table. A centrally disposed vertical axis may be adjusted between the legs of the harness in relation to the patient. The vertical axis carries the diagnostic probe which may be adjusted for individual patients. Treatment probes are offset using horizontal arms from the main shaft. The treatment modules are then hung from the horizontal arms by separate vertical shafts. The modules may move in and out toward the main shaft and may move right and left in a yaw movement or up and down in a pitch movement. Motors, preferably one for each axis, are designed to provide this movement in three degrees of freedom. The movement of the motors is controlled using a PC-based controller through a user interface. The transducers may be moved to focus the ultrasound on a single point or a series of points to cause ablation of tissues.

In order to treat deep-seated abnormalities or cancers, especially cancers of the urological organs, it is desirable to provide an automated mechanical manipulator system for controlling the movement of the HIFU transducers. By using a computer to control the movement of the transducers in a robotic system, it is possible to carefully control the location of the focused ultrasound transducer (and thereby the lesion produced by it) to ablate the tissue as indicated by the surgeon through the computer. This allows the ultrasound to be carefully controlled through a single, or a set of multiple transducers. The result is a system which has a compact work space while allowing the individual transducers to be moved independently.

During a registration process, a co-ordinate system of such data/images is transferred and related to robot and patient co-ordinates. Registration is followed by a surgical execution step, where the surgeon utilizes the pre-operative plan and is assisted by either a passive (such as a mechatronic tool to hold a device precisely in a given position), or semi-autonomous or autonomous device, such as a robot, to help perform surgical interventions.

This robotic system guides a set of transducers through a predetermined and image-guided trajectory which is set by the surgeon. In one embodiment, the transducers are each mounted on an independent module, each of which is equipped with three degrees of freedom to access any given location in a three-dimensional workspace. The procedure is guided by using a separate diagnostic ultrasound module. This diagnostic module is utilized for pre-surgical planning and may also be used to control the location of the treatment modules during the procedure.

This robotic system allows the use of either single or multiple treatment probes for organotripsy of various tissue types depending on their relative position in the body. This system may also be used for other non-invasive procedures using, for example, lasers or minimally invasive surgical tools. This system is equally suited for other imaging modalities other than diagnostic ultrasound for on-line monitoring and surgical guidance.

In order to ablate selective regions in urological organs, the use of multiple transducers is preferable for a number of reasons. This allows better access to areas which may not be safely reached along a long path alone either due to the deterioration of beam convergence along a long path or due to an access window which is partly inhibited. It also allows the production of adequate dosage using one of two modes. The first mode uses a selective overlapping focal zone by constructive interference to superimpose foci while keeping low dosage exposure in individual beam paths. Another mode is the use of individual HIFU probes or a multiple and selective combination of probes which are controlled and programmed with adequate power to result in individual lesions. This may be advantageous for a faster time of operation (due to the ability of the system to produce multiple lesions simultaneously at selected locations) or to approach larger volume target sites which may not be reachable by a single probe. Further, this arrangement allows the modulation of effective power in the focal region by independently selecting HIFU probe specifications or independently programming the dosage parameters of the probes. This renders the system to be flexible as to lesion shapes and sizes and also provides flexibility in energy distribution and minimizes the effects of non-linear propagation of ultrasound by reducing the possibility of standing waves during continuous exposure routines.

Several types of HIFU transducers have been developed for extra-corporeal, intra-cavitary and on-site/impregnated applications. The latter two can have a very selective approach for fewer targets; however, the extra-corporeal probes offer a preferred choice for completely non-invasive generic targets. The acoustic beams produced by such devices are, however, fixed in shape and in position with respect to the source. Modification of focal size can be achieved only by changing the physical properties of the source transducer (i.e., spherical shell aperture or radius of curvature, or lens dimensions or properties). A precisely controlled, mechanical manipulation system is therefore required to move the ultrasound focus (or, joint foci in case of multiple transducers) to the target location(s). The beam-shape is governed by transducer specifications, and thus is immutable during the procedure. The specific location of the tissue/organ in the human body will also affect the design of applicator systems. Based upon the dimensions, location and nature of the abnormality, the size and shape of the applicators (and thus the beam shape) can be evaluated by modeling the ultrasonic field in front of the transducers.

The principle of remote, localized tissue ablation using HIFU comprises sudden thermal necrosis in the focal lobe of the transducer due mainly to the absorption of ultrasound energy. The temperatures thus induced (60-80° C.) produce irreversible changes in the targets. Thus, instrumentation for precise and accurate targeting of the incident energy is of prime importance in order to ensure that any undesirable exposure in normal tissue is avoided. Thus, it is highly desirable to contrive a very accurate and precise positioning system for the reasons of safety due to the risk of unwanted exposure of overlying normal tissue.

Some Clinical Applications of HIFU

Renal cell carcinoma is the third most common cancer in urology and is reported to be the most common malignant tumour of the kidney. For malignant and fast growths, the tumour is resected surgically through either partial or total nephrectomy depending upon the size and location of the tumour. For experimental studies, HIFU has been used for selectively ablating the renal tissue prior to partial nephrectomy. Studies have used both extra-corporeal and hand-held laparoscopic probes for HIFU application to the kidney. In the former case, big therapy transducer skin burns were reported on the acoustic window where the applicator was placed (which could be due to the overlap of energy over the rib cage). In the latter, the intervention is not 'non-invasive' but is minimally invasive through a puncture to the target site. The average treatment time for an ablated volume of 20 cc was 45 minutes. Histopathology results demonstrated well-delineated necrosed lesions at the treatment site in the kidney. Nephrectomy, as an invasive procedure, is usually associated with significant bleeding, due to the kidney's highly vascular structure, resulting in high morbidity.

Prostate cancer is the second most common cancer and is the second leading cause of cancer-related death among men. The risk of being diagnosed with prostate cancer in one's lifetime is 1 in 14. Prostate cancer is therefore a serious public health concern. The major treatment options for prostate cancer include surgery, radiation, therapy and a combination of medical therapy with surgery or with radiation and chemotherapy. The popular surgical treatments include radical prostatectomy, transurethral resection of the prostate (TURP), orchiectomy and cryosurgery. Normally, prostate cancers/tumours are very small in size and can be found almost anywhere within the prostate volume but larger-volume tumours of the prostate are also found among older men. Surgery is associated with significant morbidity, due to blood loss with transfusion-related complications, impotence and stress incontinence. In addition, surgical intervention is not typically considered for patients whose life expectancy is less than 10 years. In a minimally invasive laparoscopic radical prostatectomy a definitive cure cannot always be achieved, and generally the treatment cannot be repeated in cases of local recurrence. In a non-invasive approach, the use of HIFU has been clinically demonstrated to destroy tissue and cure cancer without stimulating metastasis.

Frequently, the liver is the site of secondary tumours resulting from the spread of cancers from other organs, such as the colon or breast. However, primary liver cancers, also called malignant hepatoma or hepatocellular carcinoma, whereby cells in the liver mutate and form a cancerous tumour, are also frequently reported as a major health problem. Rates are highest in Asia and Africa and considered to be related to infection with the hepatitis-B virus. Liver cancer is very difficult to control unless the tumour is found when it is very small. The prevalent way to deal with liver cancer is surgical resection along with a margin area of normal tissue, and is the "gold standard" against which other treatment plans are measured. However, surgery is applicable to 10-20% of patients who present with liver cancers. In others, a combination of more than one modality is used for treating malignancies and many different types of cancers. For metastatic cancers of the liver, studies suggest the use of adjuvant methods such as ablation along with liver resection. On resection of a single lobe of the liver, the remaining other lesions can be ablated by the use of HIFU. The use of HIFU for ablating liver tissue in various study protocols has shown high potential and successful outcomes.

Testicular cancer is a malignant disease that occurs in the testes. There are two types of testicular cancer, seminoma and nonseminoma. Although it accounts for only 1% of all male related cancers, it is the most common cancer in young men aged 15 to 34. Since it presents an external site, similar to the breast tissue (both are able to spread through lymph nodes), it is a good candidate for both surgery and HIFU ablation and is curable if diagnosed at an early stage.

The ultrasound transducers which are used for treatment are coupled through an appropriate liquid such as degassed water. In another embodiment, the transducers are encapsulated in a sealed degassed water bolus with compliant bellows at one end to couple appropriate ultrasound energy with the tissue. The transducers are independently controlled to either work in coordination with each other or to function and control independent trajectories. The surgeon can control and maneuver the treatment modules in two modes either using manual or automated sequences. The end point accuracy is accomplished and tested within ±0.5 mm and the repeatability to within ±0.1 mm.

The testicular sites can be accessed using only one probe module with either a single or multiple probes mounted on to it. Kidney, liver, or lung sites can be either accessed through trans-abdominal or rib-interstices, using single or multiple probe manipulation modules and through either single or multiple routes.

Mechanical Manipulator

The mechanical manipulator 10 is shown in FIG. 1 as having a three-legged base harness with each leg 12 being connected to a central location by a top rail 14. The manipulator 10 is placed on a treatment table (not shown) on which the patient is placed. The manipulator is connected to the table at the bottom of each leg so that the base harness is locked in position. The apparatus (not shown) for fixing the legs to the table may either be a simple screw arrangement, or may involve a sliding arrangement mounted on a track on the table (partially shown in FIG. 7). A main shaft 18 carries the various probes that are mounted on the manipulator. These are connected through a central positioning device 16 which may be movable from side to side along the top rail 14 as needed to adjust for individual patients. When it is adjusted for a patient, it is locked into position for the entire procedure.

A diagnostic module 24 is suspended, typically, centrally from the main shaft 18. The diagnostic module contains a diagnostic ultrasonic probe, which is used for imaging the area of interest. The probe defines a traditional ultrasonic picture for the surgeon to review at the graphical user interface of the computer. When adjusting, for instance, a generic sector type diagnostic probe in a diagnostic module for an individual patient, it is roughly adjusted manually (sector direction) using manually adjustable dial 26. The dial provides an orientation of the sector plane so as to set the initial reference images. A motorized linear movement in the horizontal direction is then provided to the diagnostic module such that two-dimensional images parallel to the reference image can be obtained. Once this is set for an individual patient, further movement is controlled by way of the computer and a precision slide motorized translation system 28.

The main shaft 18 also carries horizontally extending arms 20, with one arm for each treatment module. On each horizontally extending arm 20, a vertical shaft 22 extends downwardly. The horizontal arms are movable through an angle e and individual shafts 22 are locked into vertical position using screws or other means. Each transducer module 30 is mounted at the end of a vertical shaft 22. The length of each vertical shaft from the corresponding horizontal arm 20 will differ by a constant offset since the horizontal arms are stacked vertically to allow independent movement.

The transducer modules 30 are detachable at the central shaft such that only a selected number of HIFU transducers need be mounted. The computer program that controls these modules is also written in a modular fashion and the number of participating modules are defined by the user in the beginning through the graphical user interface. Thus, in the case of only a selected single transducer module, the control problem is simplified to coordinated control with only the diagnostic module (non-coordinated control with other treatment modules). Within a given transducer module, the various axes are mechanically de-coupled, further simplifying the control strategy and thus introducing enhanced safety.

Figure 2:
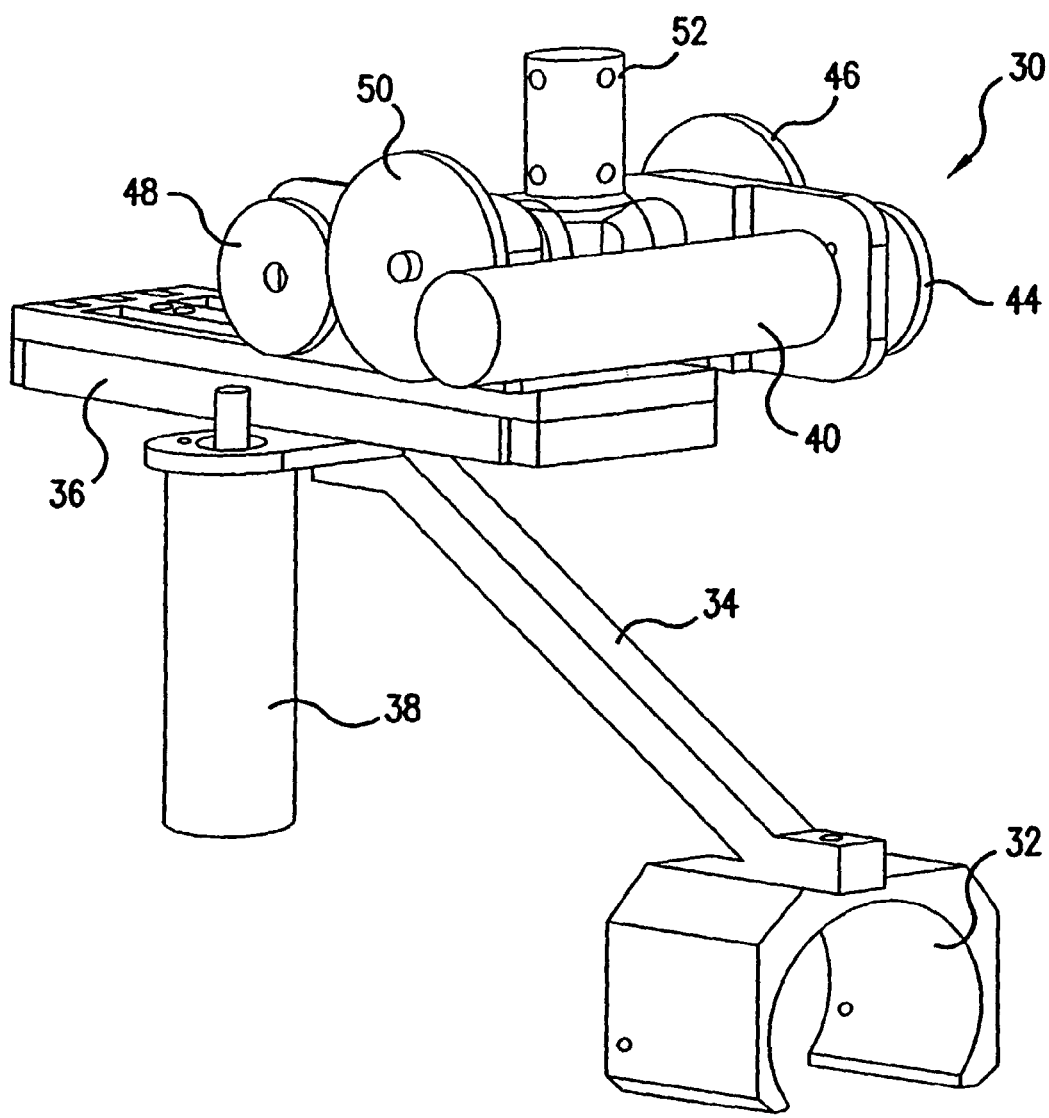
FIG. 2 is a perspective view of a first embodiment of the treatment module of the present invention.

FIG. 2 shows a first embodiment of a treatment module 30. A transducer holder 32 contains an opening, which is typically cylindrical, into which the ultrasonic transducer may be placed. Screws or other fastening means may be inserted through the sidewalls of the holder in order to maintain the transducer in its proper location. The transducer holder 32 is connected to the rest of the module through an angled bar 34. This bar extends the holder and transducer away from the moving parts of the module so as to avoid any interference. The size, shape, strength and disposition of the bar may be varied as long as it provides a stable structure for holding the probe holder.

Each module includes a base plate 36 on which the motors of the module are mounted. Motor 38 is used to drive probe holder 32 in a forward and backward direction. Motor 38 includes a pinion (mounted on the motor's shaft) which interacts with a rack provided on the edge of base plate 36. The motor 38 and bar 34 are connected on the bottom side of the base plate 36 on a slide plate (not shown) which slidingly moves along the bottom of the base plate 36. When the motor 38 drives the pinion to move along the rack, the slide plate slidingly moves along the longitudinal direction of the base plate 36, thus carrying bar 34 and probe holder 32 in a similar direction.

Figure 3:
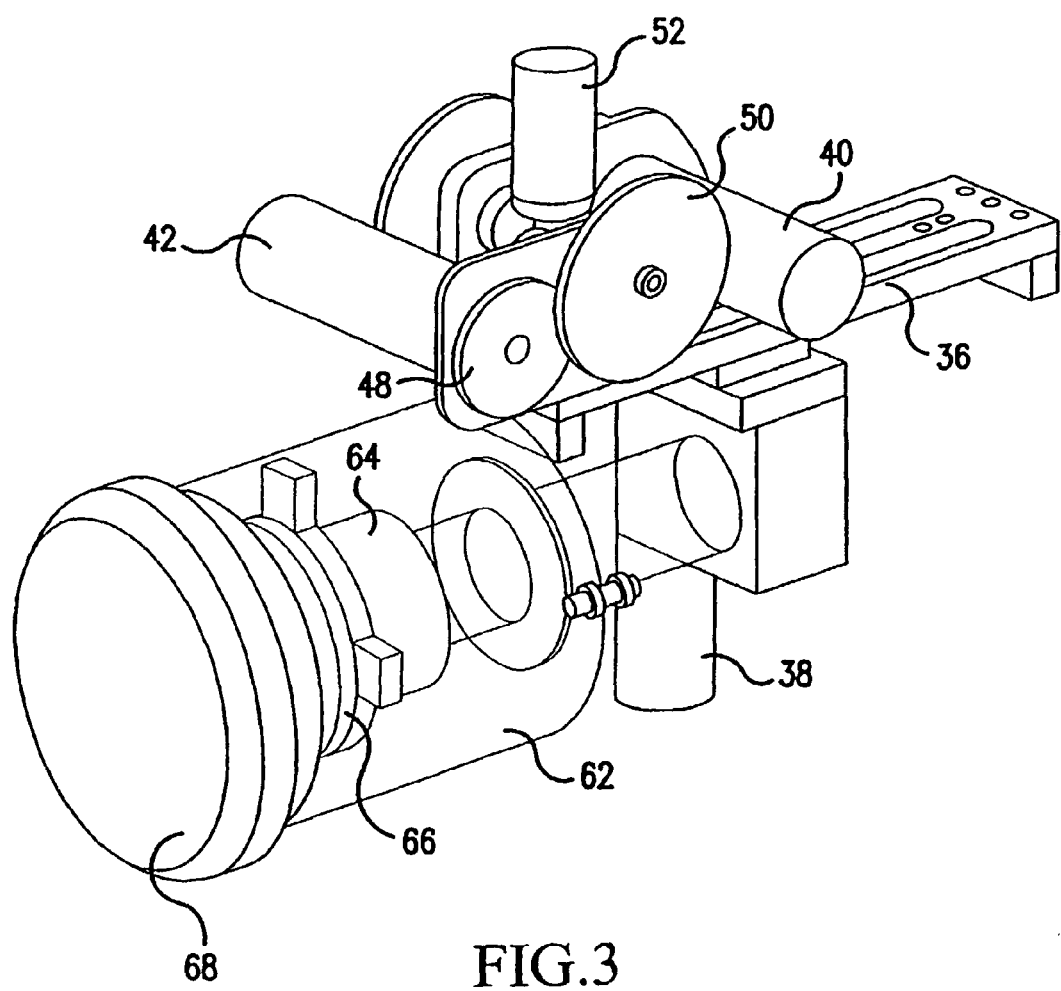
FIG. 3 is a perspective view of a second embodiment of the treatment module of the present invention.
Figure 4:
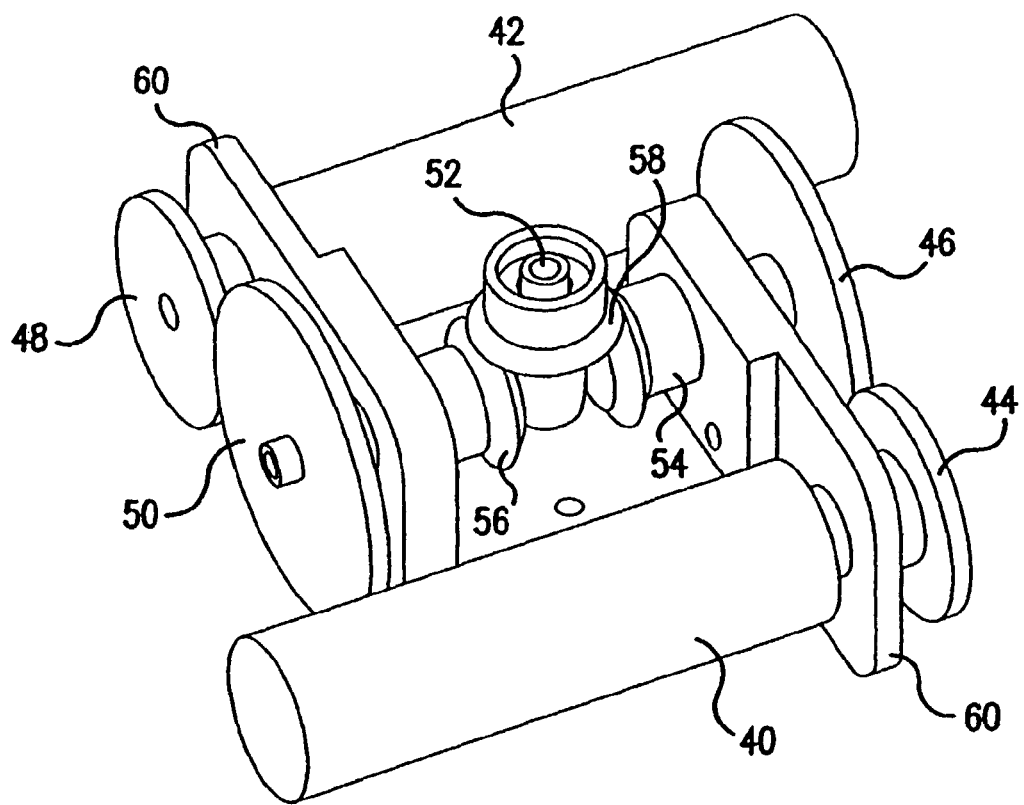
FIG. 4 is an upper view of the treatment module of the present invention.

The mechanism for making yaw (right-and-left) and pitch (up-and-down) movement is contained on the top of the base plate 36. This mechanism is shown in FIGS. 2, 3 and 4. Motors 40 and 42 have a gear 44 and 48, respectively, connected for rotation. These gears interact with spur gears 46 and 50. The spur gears are connected through axles (unnumbered) which extend toward each other. Miter gears 54 and 56 are fixedly mounted on these axles and move along with the spur gears. The miter gears have a 45° angle which interacts with central miter gear 58 having a similar shape. These gears and motors are mounted on frame 60, which is connected to the base plate. Vertical shaft 52 is fixedly connected to vertical shaft 22 to support the entire module from the base harness.

In order to accomplish a yaw motion, motors 40 and 42 cause miter gears 54 and 56 to move in the same direction (i.e., clockwise or counterclockwise) about the fixed central miter gear 58. As miter gears 54 and 56 advance around the fixed central gear, the entire frame 60, and hence base plate 36, on which they are mounted moves in a clockwise or counterclockwise direction about central miter gear 58. Thus, the yaw movement is about an axis aligned with vertical shaft 52.

In order to cause a pitch motion, miter gears 54 and 56 are driven by motors 40 and 42 in opposite directions in relation to fixed central miter gear 58. These gears will then not move since they prevent each other from moving about the central miter gear. This causes the axles on which they are mounted and the spur gears 46 and 50 to also not move. The rotation of the motors then causes gears 44 and 48 to "climb" around spur gears 46 and 50, respectively, with one of the gears 44 and 48 moving up and the other down. This forces the frame 60 to pivot up or down about an axis aligned with the axles between the spur gears.

Thus, depending on the direction of movement of motors 40 and 42, the frame 60 is moved in a yaw or pitch movement. This causes base plate 36 to likewise move since the frame 60 is connected fixedly to the base plate 36. This also moves the slide plate on which bar 34 and holder 32 are mounted to likewise have a pitch and yaw movement so that the transducer is similarly moved. All three motors are driven under the control of the computer, which determines the amount and direction of the movement.

By utilizing this arrangement, the transducers are arranged with independent modules which allow three degrees of freedom so that the probes can be positioned and oriented in the desired three-dimensional coordinates. When multiple probes are used, the modules are identical for ease of manipulation. The specific target defines the number of the modules and their control. The motors which are utilized are typically DC servo motors although any appropriate motor arrangement can be utilized.

The modules may be individually set in position manually for a given patient. All the joints are back-drivable and encoders, which are normally driven by the motors while the modules are being moved are also moved while they are manually set. Accordingly, the computer is aware of the actual position of the modules at all times by counting pulses from the encoder so that the position of the modules is always maintained. It should further be noted that the zero point for each of the modules may be defined as horizontal and aimed at the vertical axis (and is also mapped to the "origin" axes on the reference image). Thus, it is simple to determine the position of the transducer.

The zero point may be calibrated using a number of different mechanisms. Thus, it is possible to utilize a laser mounted on the transducer or the transducer holder which is aimed at a specific zero point to determine that location. It is also possible to install a bracket or other mechanical device with markings to determine the zero point location.

FIG. 3 shows a second embodiment of the treatment module. In this embodiment, the HIFU transducer is encapsulated in a degassed water bolus. The bolus includes a hollow Perspex cylinder 62 in which is mounted a tubular holder 64 which is coupled to a three-axial wheel ring 66. The housing is water tight and has a flexible bellow 68 at the front end in order to have a compliant coupling with the tissue. The probe holder is linearly displaced inside cylinder 62 in a piston arrangement. The other movements are similar to those shown in the embodiment of FIG. 2.

An alternative arrangement of the motor system places the yaw and pitch controls in a different arrangement. The linear movement remains similar to that discussed above. However, the yaw arrangement is accomplished by placing a motor directly in line with the probe holder (mounted to the motor shaft) so that the motor horizontally moves the transducer directly. The pitch arrangement is made by mounting a motor on the slide plate, with the output of the motor driving a shaft on which the probe holder and yaw motor are mounted. Since the motors which are utilized weigh a little as 200 grams, movement is accomplished easily.

Figure 5:
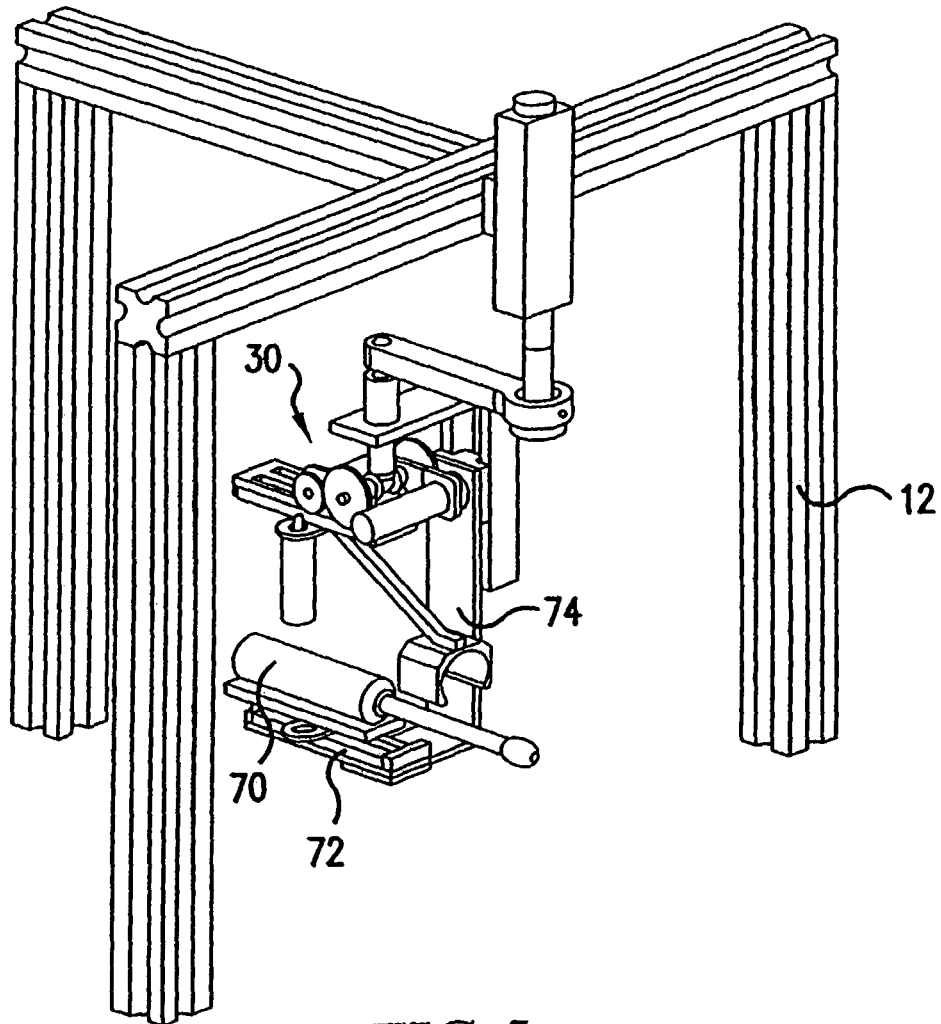
FIG. 5 is a perspective view of a second arrangement of modules according to the present invention.

FIG. 5 shows another embodiment of the base harness. In this case, the tripod arrangement is similar. However, the diagnostic module 24 is replaced with a different diagnostic module. In this case, the module carries a trans-rectal arrangement which may be moved horizontally using mechanism 72 which moves forward and backward. The forward and backward movement is controlled in a similar fashion to the linear movement caused by motor 38. The vertical positioning can be accomplished using linear mechanical guide 74. This is set according to the position of the patient and his size. The control of the treatment module 30 remains the same.

Figure 6:
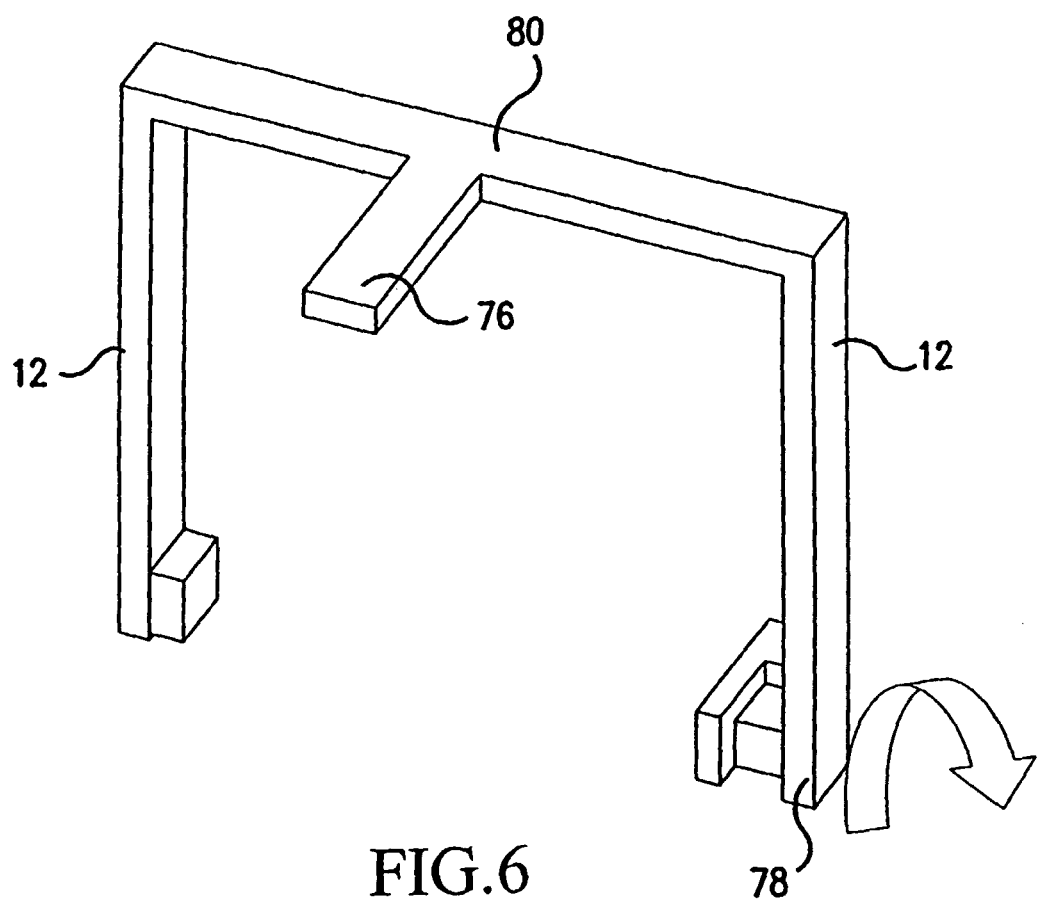
FIG. 6 is a perspective view of a two-legged base harness according to the present invention.

FIG. 6 shows another embodiment of the base harness. In this embodiment, only two legs 12 are utilized. In this embodiment, the lower end of the legs are fixed to the table, but rotatable, so that the harness may be tilted at an angle to the table when desired. Thus, for any particular part of the treatment, the harness is fixed in its position but may be rotated if two different angles are necessary for the same patient. Accordingly, the holder 78 may be fixed to the table with an adjustable rotating mechanism which may be selectively utilized when needed. In this harness system, a connection point 76 is still provided for the various treatment modules. However, an additional connection 80 for a second group of modules is also provided in a different location on the top bar.

Figure 7:
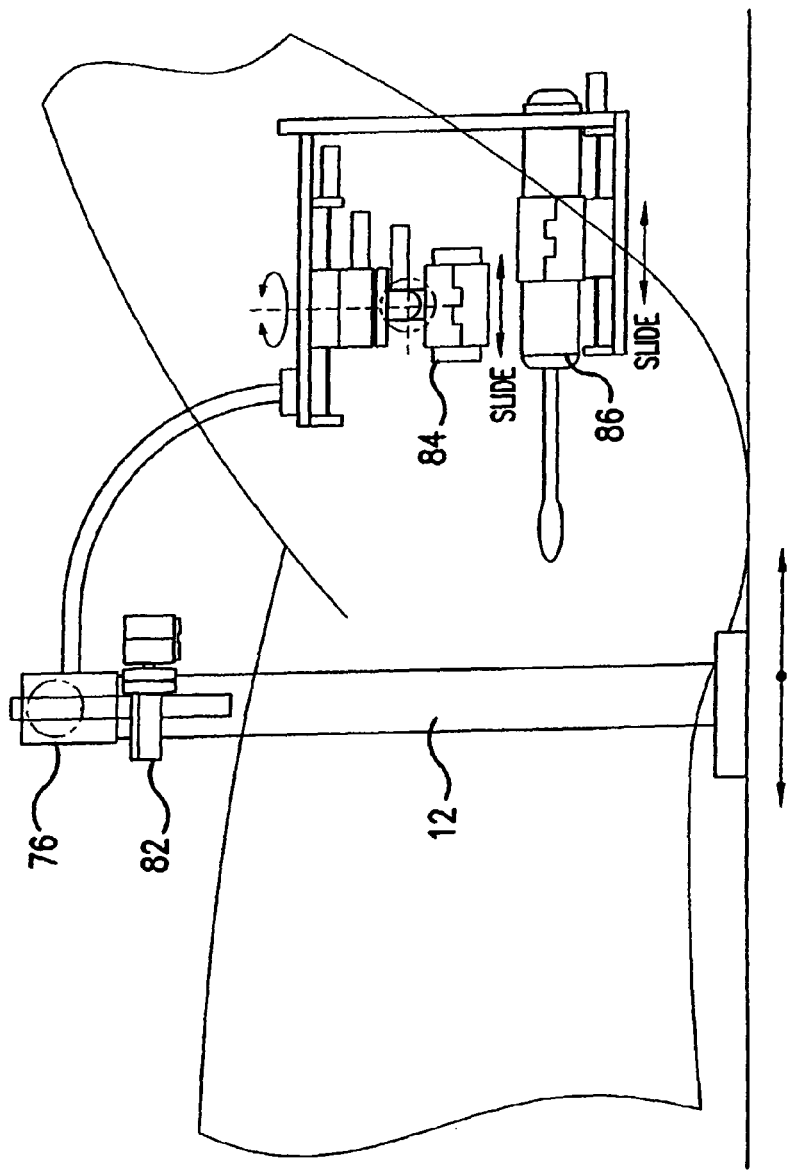
FIG. 7 is a diagram showing movement of the harness of FIG. 6.

Thus, in this configuration, the modules are mounted from the central swivel mount 76 as in the previous designs. However, to facilitate better access to certain remote organs, an additional rotational motion is provided through the lockable swivel heads 78 at the base of the legs where they are mounted to the surgical table. Thus, this arrangement can be used with treatment modules arranged for trans-perineum and supra-pubic access or for a trans-rectal diagnostic module to provide multiple route applications or for the prostrate for example. FIG. 7 shows the use of the two-legged configuration of the base harness used to couple two treatment transducers, one in a supra-pubic 82 arrangement and one in a trans-perineum 84 arrangement along with a trans-rectal 86 diagnostic probe. This provides a multiple route application to the prostate, for example.

Another possible design for a plurality of HIFU transducers is to utilize a single jig on which a plurality of transducers are mounted. The transducers may be mounted so as to be fixed in regard to each other and the jig. The jig may then be mounted on a treatment module having three degrees of freedom or other possible movement arrangements. Thus, the transducers may be moved in three directions but remain fixed in relation to each other. This type of arrangement can be used where multiple transducers are advantageous, but where it is not necessary to individually aim the transducers. This may be in the case where a large acoustic window to the target is available or where the target is externally accessible such as in breast and testicular sites.

Surgical Planning

The mechanical system described above is controlled using an electronic interfacing hardware with a PC having controller cards and specially designed hardware that interfaces and controls the system. The typical lesion dimensions produced by a single or multiple probes may not be able to cover the entire volume of the desired target region. It is necessary to mechanically scan the superimposed foci mutually over the entire tissue of interest. The treatment is to be carried out by means of a suitable exposure duration of the HIFU beam (at a selected power/intensity level) at one spot following a scanning motion of the probes and subsequent exposure until the entire volume of the lump is covered in a three-dimensional manner.

Figure 8:
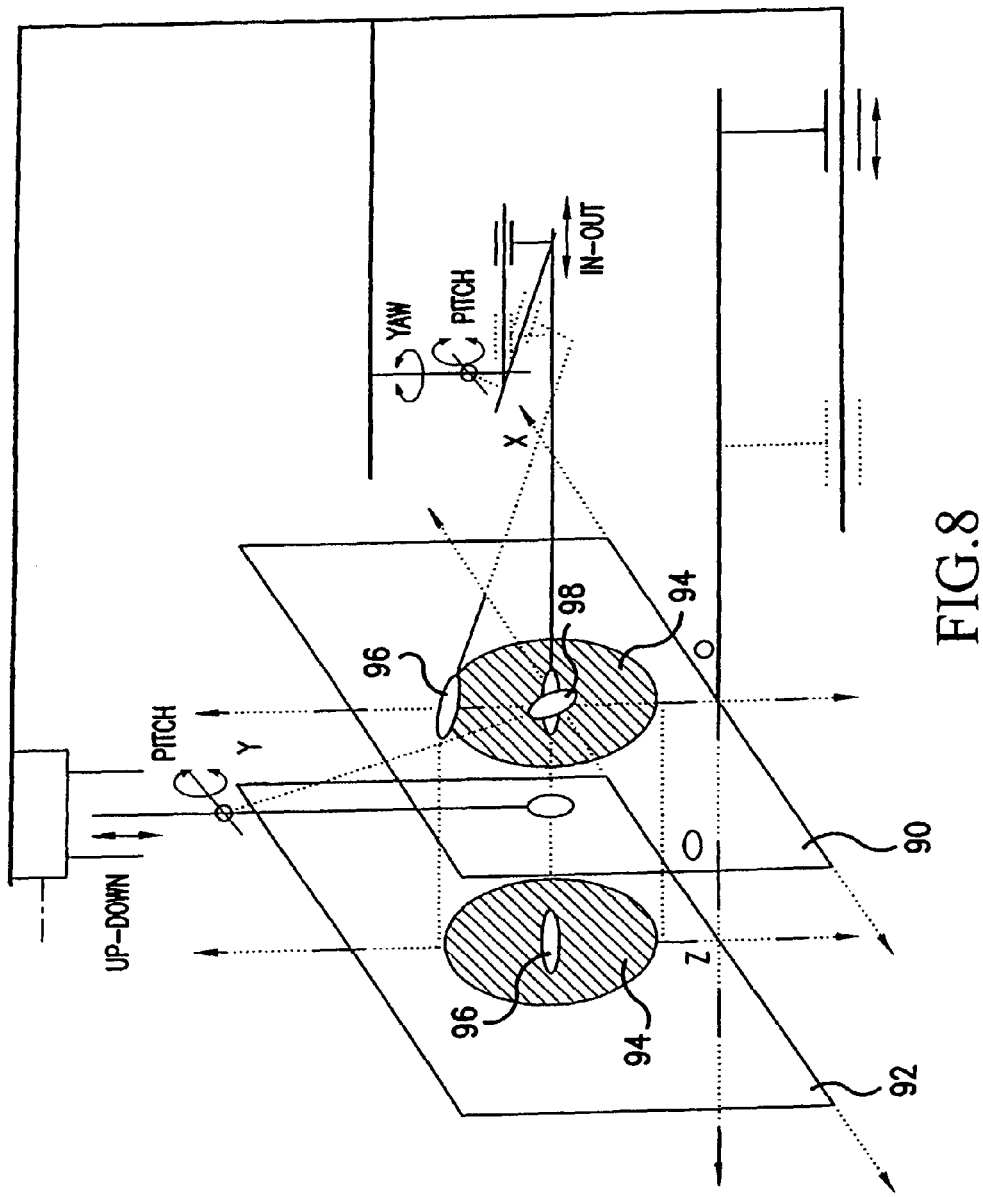
FIG. 8 is a diagram showing the focus of the ultrasonic transducers and their movement in the arrangement of FIG. 7.

FIG. 8 shows the kinematics of the arrangement shown in FIG. 7. The image data acquisition is programmed using an image grabber card (MATROX, Meter II). The diagnostic module holds and guides the diagnostic ultrasound probe linearly (in-out) for tumor localization, registration and volume calculation as well as real time imaging. Parallel image frames 90,92 are perpendicular to the trans-rectal diagnostic module and are placed at an index distance with respect to the probe. This is effected using the horizontal translation arrangement 72 (FIG. 5). The reach of the translatory motion is restricted by a sufficient number of images to cover the target region in three-dimensional space. The pitch and yaw axes of the trans-perineum module define a circular work space 94 on each image, thus resulting in a cylindrical workspace (along with linear movement of diagnostic probe head during the procedure), whose central axis coincides with the central axis of the image frames. The images are also registered with other treatment modules if multiple modules are being utilized. Based on the dosimetry and surgical protocol, a typical lesion size is estimated in a given tissue using a priori knowledge. The HIFU lesion 96 is cylindrical in shape (with variable diameter along the axis-oblate/cigar shape) and the length of the lesion determines the required index distance between the images while the diameter determines the inter-lesion distance in a given two-dimensional frame. In case of multiple treatment modules, the resulting lesions 98 are produced by the overlap of multiple beams at the probe foci. The image coordinates are thus related to robot coordinates in the pre-operative stage and translated intra-operatively.

An interactive interface is designed for allowing the clinical users to employ surgical protocols of choice under selected controls. The HIFU transducer system seeks its reference target spot by accessing on-line data from the diagnostic scan module. During the pre-planning phase, images of target tissue are captured in a given direction with a given index. Tumor boundary points are defined (using a mouse cursor) and the tumor volume is calculated for defining dosage parameters.

A further discussion of the surgical planning and determination of the dosage can be seen in published International Application WO03/059434, published Jul. 24, 2003. The discussion there further indicates the planning stages used for the diagnostic probe in preparation for the activation and control of the treatment transducers.

Figure 9:
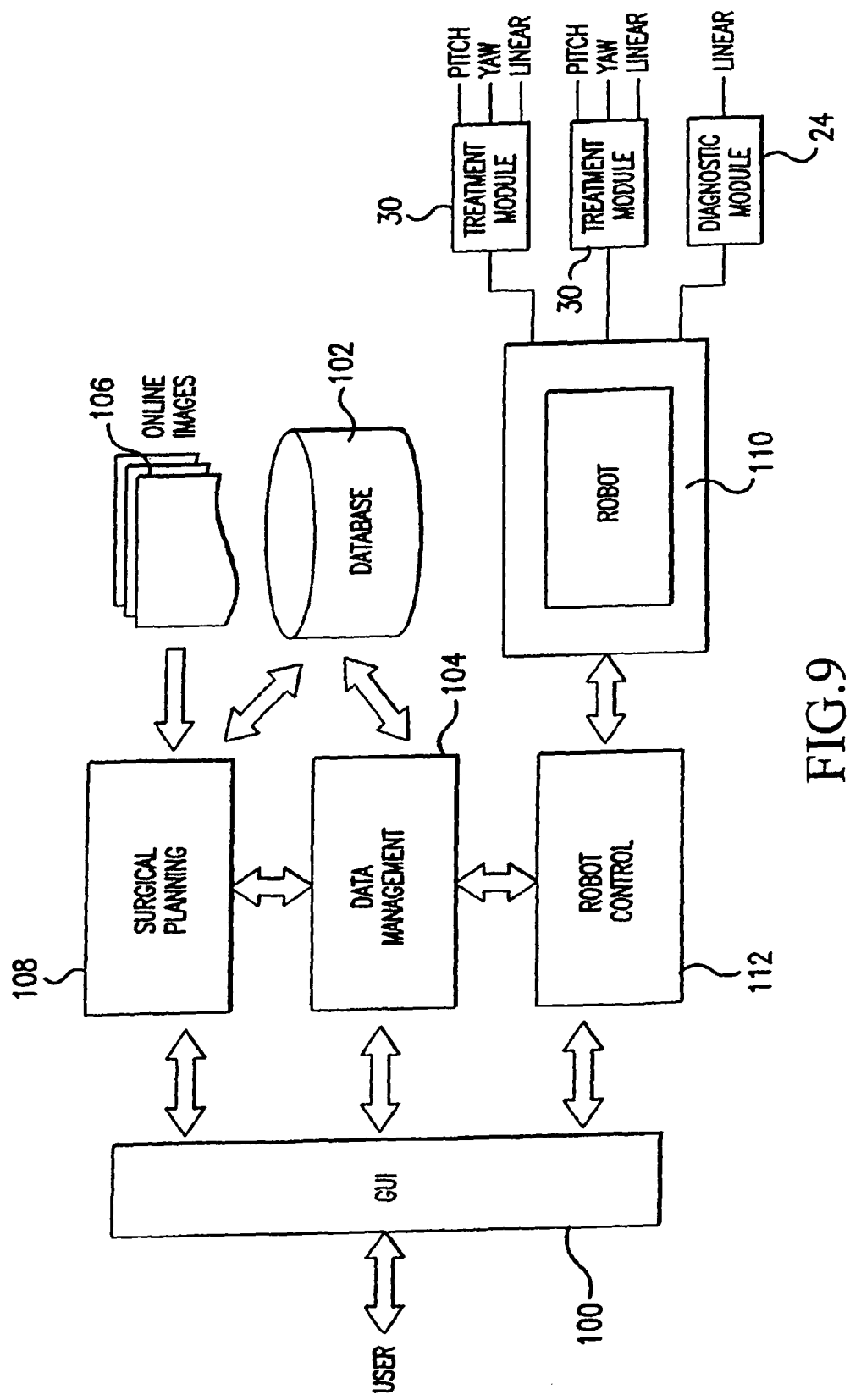
FIG. 9 is a schematic of the robotic controls for controlling the movement of the modules.

The control interface is shown in FIG. 9. The control software is written using an object-oriented software design methodology and implemented using Microsoft Visual C++ and open GL. GUI 100 shows an on-line image view and system menu and activates the corresponding detail functions. The two functions of the control module, namely the image guided surgical planning and robot control can be implemented as a separate tab in a function interface shown to the user. All the prime axis movements are displayed on the screen and are registered with the image display.

The graphic user interface 100 is connected to a data base 102 through a data management section 104 in order to store and retrieve data. This information is combined with the on-line images 106 by the surgeon in a surgical planning section 108. The robot 110 is controlled through the robot control section 112 which relies on input from the interface 100 (the surgeon) and the data management section 104. The robot in turn controls the diagnostic module and treatment modules 24 and 30 in terms of their movement which can be a linear movement for the diagnostic module and movements in the pitch, yaw and linear directions for the treatment modules in order to reach all the positions within the boundary marked by the user/surgeon (during the data acquisition and surgical planning phase).

System Control

The intent of using a robotic motorized system is to automatically position and register the HIFU and diagnostic probes with respect to each other and with respect to the patient precisely, in a desired configuration. The functionality of the control module comprises three basic functions: Image guided surgical planning (as explained in the above section), Robot control and trajectory planning and HIFU dosage control.

Robotic manipulation of various system modules is governed by a PC-based controller (Galil, DMC 1842) using API programming for motion control. Three 4-axis PC based controller units govern various sub-modules of the system within a pre-defined and constrained work envelope. As various independent probes are required to align to one point, the kinematics constraints include coordinated motion. The control software is written using an object-oriented software design methodology and implemented using, for example, Microsoft Visual C++.

Once the surgical protocol is decided in the pre-planning phase, and a manual or, auto mode selection is chosen, the robot accurately positions all the transducers at specified locations such that the con-focal region is coincident with the planned lesion position on a given image. The data that are managed by the control module includes the robot initialization, positional information, such as the position of treatment modules and diagnostic module at a given instant and safety control information (by reading limit switches and sensors).

The user is allowed to select target areas on subsequent 2-D images and the selected protocol can be replayed either in manual or auto mode. In the former case, the user selects the location of making a lesion on the on-line image with the help of a cursor selection. The selected position in the image is automatically translated to robot coordinates using inverse kinematics calculations. Geometric and graphical modules/solutions to inverse kinematics are used for this purpose (15-17). On confirmation of the position again the user prompts to position the chosen transducers by pressing a control on the GUI for the robot to move. This sequence is repeated for all the desired target points in a 2D frame one by one and then in consequent frames, thus ablating a given target volume in 3-D. However, in the auto mode, lesion margins and indices are defined and the target boundary points in respective 2D images are selected. The locations and sequences thus entered are stored in memory and by pressing the play button, the robot replays and positions the transducers automatically at those locations and delivers a pre-defined thermal dosage.

The data that are managed by HIFU-Dosage control module includes surgical planning information such as protocol settings, thermal dosage calculations, frequency of operation of transducers, power in each beam, time of exposure at each location, and off-time between two consecutive exposures. A zero off-time would result into continuous exposure, which may be favorable in certain applications. However, in point to point manipulation applications HIFU dosage delivery control and robot control are decoupled as a safety strategy so as to avoid any interference and unintended exposure during manipulation. The system allows remotely controlled independent parametric selection to participating HIFU probes in selective protocols where power modulation and flexibility in shape and size of the lesions presents an advantage for tissue ablation. Also, the simultaneous and individual or hybrid operative modes present flexibility in treatment protocols and operating time.

Since this apparatus is being used in a medical situation, it is imperative that safety measures be incorporated into the system. One safety measure is set at the software level where all of the maximum limits are set to prevent the robot from going beyond the boundary of each probe workspace. The second safety system is the hardware with emergency safe recovery. In any instance of operation, the emergency condition can be called upon either by the software emergency button or by a hardware emergency switch or sensor safety routine. In the emergency condition, all of the axes are switched off automatically. During this time the computer stores all the positional information so that it can reposition itself automatically once the emergency is resolved.

The present invention thus discloses a fully automated robotic system designed, developed and tested for clinical applications, which incorporates pre-surgical and on-line planning and precise motorized control of HIFU transducers. The system's flexibility is especially advantageous in urological applications. The robotic system is modular in design and has provisions for both single and multiple route access to the target sites for independent and coordinated superimposed exposure. The robotic system has been tested on laboratory phantoms and on in vitro and ex vivo tissues such as excised kidneys with very precise outcomes and high reproducibility. The robotic system has also been tested for functional validation and the end-point uncompensated accuracy is accomplished within ±0.5 mm (compensated accuracy is within ±0.1 mm) while the repeatability is recorded quite high, within 0.1 mm.

The robotic system overcomes the problem with conventional HIFU transducers (which are fairly big, at around 10 cm in diameters) by providing a design that incorporates the use and independent control of multiple probes. The angular configurations for participating probes are chosen such that constructive interference at the superimposed foci and destructive interference in the beam path provide for trackless lesioning and thus minimizes damage to surrounding normal tissue.

The ability to manipulate multiple HIFU probes to target a selected region from multiple routes allows for better targeting of remote tissue. The invention provides distinct advantages especially for applications in following scenarios:

(a) Prostate

The ability to target the tumor site from the trans-perineum route and one or more supra-pubic routes renders the system with maximum maneuverability (flexibility) to reach all possible target tumor sites, as opposed to the limited motion inside the rectal cavity in the case of trans-rectal systems. The robotic techniques unique to this system also render high accuracy, repeatability and precision to the positioning and localizing ability. Trans-rectal burns are also observed frequently in other current systems, partly due to the energy attenuation being very closely positioned with the rectal skin, which represents a thick and highly attenuating medium. The system of the present invention overcomes that problem by avoiding trans-rectal route and/or fractionating the energy into multiple low power beams/routes, thus resulting in minimum damage to the overlying skin and other normal tissue.

(b) Kidney and Other Organs with Trans-Abdominal Reach

With the precise robotic techniques afforded by the present system, the multiple probes can be extra-corporeally and precisely positioned and maneuvered in between the rib interstices. This provides advantages over the current systems using large single spherical or paraboloid HIFU applicators, which limit the target region that can be treated and which can also be intercepted by bone. The present system is also an improvement over the current laparoscopic renal ablation systems, which is an invasive technique.

Furthermore, the robotic system utilizes inexpensive on-line ultrasound imaging for guidance of the probe-positioning and controlling robotic trajectories inside the remote target, as opposed to on-line MRI imaging as used in some commercial systems.

INDUSTRIAL APPLICABILITY

The subject mechanical manipulator may be used in medical treatment environments.

The following references are cited in the present specification. Each is hereby incorporated by reference in its entirety and for all purposes.
1. Chauhan, S. (1999) 'The Applications Of HIFU And Robotic Technology In Surgery', Phd Thesis (Medical Robotics), Imperial College Of Sc. Tech. And Med. 1999.
2. R. H. Taylor, Et Al. An Image-Directed Robotic System For Precise Orthopedic Surgery IEEE Trans. On Robotics And Automation, 10(3):261-275, 1994.
3. Davies, B. L, Chauhan, S and Lowe M. J A Robotic Approach to HIFU Based Neurosurgery. Lecture Notes in Computer Science 1496, pp. 386-396. Springer Verlag, October, 1998
4. Sunita Chauhan, A Mechatronic System for Non Invasive Treatment of the Breast Tissue, Mechatronics and Machine Vision 2002: current Practice, 359-366, Research Studies Press Ltd.
5. F. Tendick, and M. C. Cavusoglu, Human Machine Interfaces for Minimally Invasive Surgery. In Proceedings of the 19th Annual International Conference of the IEEE Engineering in Medicine and Biology Society (EMBS'97), Chicago, Ill., Oct. 30-Nov. 2, 1997, pp. 2771-2776.
6. Simon, D. A., B. Jaramaz, et al, Development And Validation Of A Navigational Guidance System For Acetabular Implant Placement, Proceedings of the First Joint CVRMed/MRCAS Conference, 583-592, 1997.
7. Hynynen, K. (1987), Roemer, R. Et Al, 'A Scanned, Focused, Multiple Transducer Ultrasonic System For Localised Hyperthermia Treatments' Int. J. Hyperthermia, 3(1), 21-35.
8. T. Uchida, N. T. Sanghvi, T. Satoh, A. Irie, T. Omata, S. Baba, M. O. Koch, And T. A. Gardner, "Transrectal High Intensity Focused Ultrasound For The Treatment Of Localized Prostate Cancer," Proc. Of The International Symposium On Therapeutic Ultrasound, 2002, Pp. 8-16.
9. Watkin, N. A. (1995), G. R. Ter Harr, Et. Al 'The Urological Applications If Focused Ultrasound Surgery' British J. Of Urol., Vol. 75, 1-8.
10. Ralph V. Clayman, From Knife To Needle To Nothing: The Waning Of The Wound, Brazilian Journal Of Urology Official Journal Of The Brazilian Society Of Urology, Vol. 27 (3): 209-214, May-June, 2001
11. Kenneth Ogan And Jeffrey A. Cadeddu, Minimally Invasive Management Of The Small Renal Tumor: Review Of Laparoscopic Partial Nephrectomy And Ablative Techniques, Journal Of Endourology, November 2002, Vol. 16, No. 9: 635-643
12. Aarnink, Rene G et al., Transrectal Ultrasound Of The Prostate: Innovations And Future Applications. Journal Of Urology. 159(5):1568-1579, May 1998.
13. Haecker, M. S. Michel, P. Alken, K. U. Köhrmann, S. Chauhan, Multiple focused probes for High intensity focused ultrasound: An experimental investigation, 20th World Congress on Endourology and Shockwave, 19-22 Sep. 2002, Genoa, Italy.
14. Sunita Chauhan, M. S. Michel, P. Alken, K. U. Köhrmann, A. Haecker, High-intensity-focused-ultrasound (HIFU) induced homeostasis and tissue ablation, BiOS'03, Photonics West, SPIE, 25-31, Jan. 2003, 4954-25, San Jose, USA.
15. John Craig, Introduction to Robotics: Mechanics and control, Prentice Hall, 2005, ISBN 0201543613
16. Angeles, Jorge, Fundamentals of robotic mechanical systems: theory, methods, and algorithms Springer, Pub Date: 2003: ISBN: 038795368X
17. Pfalzgraf: "On Geometric and Topological Reasoning in Robotics". Annals of Mathematics and Artificial Intelligence 19 (1997) 279-318 (special issue on AI and Symbolic Mathematical Computing), Jacques Calmet, John A. Campbell (Eds.).

What is claimed is:

1. A mechanical manipulator for moving HIFU transducers comprising:
a base harness;
a main shaft mounted on said base harness;
a diagnostic module mounted on said main shaft;
at least one treatment module mounted on said main shaft via a vertical shaft, said at least one treatment module being pivotably movable about the main shaft;
said at least one treatment module comprising a probe holder for receiving a HIFU transducer; and motors,
wherein the motors, each independently of any other, are configured to move said probe holder through three different directions including a pitch movement about an axis orthogonal to the vertical shaft, a yaw movement about an axis aligned with the vertical shaft and a linear movement toward and away from said main shaft.

2. The manipulator according to claim 1, further comprising a horizontal arm mounted to the main shaft for rotation in a horizontal plane about the main shaft, wherein the vertical shaft is connected to the horizontal arm, and said at least one treatment modules is mounted on the vertical shaft.

3. The manipulator according to claim 2, wherein said treatment modules are mechanically detachable from said main shaft.

4. The manipulator according to claim 1, wherein said at least one treatment module further comprises:
a connecting structure movably connected to the vertical shaft, the motors and the probe holder being mounted to the connecting structure;
a central miter gear fixedly connected to the vertical shaft; and
a pair of miter gears connecting to the connecting structure and engaging with the center miter gear respectively.

5. The manipulator according to claim 4, wherein two of the motors drive the pair of miter gears to interact with the central miter gear, and the interaction between the pair of miter gears and the central miter gear is configured to cause the yaw and pitch movements of said probe holder.

6. The manipulator according to claim 4, wherein when the pair of miter gears are driven by the motors to move in the same direction with respect to the central miter gear, the probe holder is moved in the yaw movement, and when the pair of miter gears are driven by the motor to move in opposite directions with respect to the central miter gear, the probe holder is moved in the pitch movement.

7. The manipulator according to claim 1, further comprising a motorized slide connecting to the main shaft, wherein said diagnostic module is moved horizontally along the motorized slide.

8. The manipulator according to claim 1, wherein said base harness includes three legs and a top rail connecting at least two of said legs, on which said main shaft is mounted.

9. The manipulator according to claim 8, wherein said base harness is mounted on a treatment table.

10. The manipulator according to claim 9, wherein the base harness is mounted on said treatment table using a slide arrangement.

11. The manipulator according to claim 1, wherein the base harness has two legs and a top rail extending therebetween, with said main shaft being mounted on said top rail.

12. The manipulator according to claim 11, wherein the base harness is mounted to a treatment table so as to allow for rotation of the base harness at an angle to the table surface.

13. The manipulator according to claim 1, wherein said diagnostic module and said treatment modules are controlled for movement by a computer.

14. The manipulator according to claim 13, wherein the diagnostic module and the treatment modules respectively comprise encoders, the encoders being configured to send location information to said computer for determining locations of the diagnostic module and the treatment modules.

15. A mechanical manipulator according to claim 1, wherein at least one of said treatment and said diagnostic modules comprises:
   a probe holder;
   a connecting structure attached to said probe holder;
   a base plate connected to said connecting structure;
   a first motor for moving said probe holder and connecting structure longitudinally along said base plate; and
   second and third motors for causing yaw and pitch motions of said module;
   a frame holding said second and third motors on said base plate;
   a vertical shaft connected to said frame and connected to the main shaft of said mechanical manipulator.

16. The mechanical manipulator according to claim 15, wherein said vertical shaft carries a central miter gear and said second and third motors drive miter gears on opposite sides of said fixed miter gear for yaw motions.

17. The mechanical manipulator according to claim 15, wherein said second and third motors drive spur gears on opposite sides of said frame causing a pitch motion of said module.

18. The mechanical manipulator according to claim 15, wherein said first motor and said connecting structure are mounted on a linear slide which is mounted on said base plate, said base plate having mounted thereon a rack for engagement with a pinion mounted on said first motor.

19. The mechanical manipulator according to claim 15, wherein said second motor is mounted on said connecting structure for yaw movement of said probe holder.

20. The mechanical manipulator according to claim 19, wherein said third motor is mounted on said base plate for moving said connecting structure, said first motor and said probe holder in a pitch motion.

21. A computer controlled manipulator for HIFU transducers comprising:
   the mechanical manipulator of claim 1,
   each of said diagnostic modules and treatment modules having three motors for moving said probe holder in three degrees of freedom, said motors being controlled by said computer;
   and further comprising a computer electrically connected to said diagnostic module and treatment modules for control of movements of said motors of said diagnostic and treatment modules;
   each of said treatment modules having a probe holder for mounting a HIFU transducer;
   whereby said computer controls movement of said probe holders to direct ultrasonic outputs from said HIFU transducers.

22. The manipulator according to claim 21, wherein the ultrasonic outputs from said transducers are used to ablate tissues in a medical treatment and excitation parameters are controlled by said computer.

23. A manipulator according to claim 21, wherein the diagnostic module provides an image through said computer for a surgeon to locate an area for treatment and direct movements of said transducers to act on said area of treatment.

24. The manipulator according to claim 21, wherein each of said modules includes encoder for determining positions of said modules and communicating the positions with the computer.

25. A method for directing ultrasonic outputs of HIFU transducers, comprising:
   providing a diagnostic module and at least one treatment module comprising a HIFU transducer mounted on a mechanical manipulator;
   selecting an area for treatment using an image from said diagnostic module;
   directing a computer to control the aiming of said HIFU transducers;
moving said treatment modules by combined linear translation, and at least one of pitch and yaw movements, to direct said output of HIFU transducers to said area for treatment, by controlling motors on said modules through said computer, the mechanical manipulator comprising:
   a base harness;
   a main shaft mounted on said base harness;
   a diagnostic module mounted on said main shaft;
   at least one treatment module mounted on said main shaft via a vertical shaft, said at least one treatment module being pivotably movable about the main shaft;
   said at least one treatment module comprising a probe holder for receiving a HIFU transducer; and motors,
   wherein the motors, each independently of any other, are configured to move said probe holder through three different directions including a pitch movement about an axis orthogonal to the vertical shaft, a yaw movement about an axis aligned with the vertical shaft and a linear movement toward and away from said main shaft.

* * * * *